US010126111B2

United States Patent
Levitz

(10) Patent No.: US 10,126,111 B2
(45) Date of Patent: Nov. 13, 2018

(54) ASSOCIATING OPTICAL COHERENCE TOMOGRAPHY (OCT) DATA WITH VISUAL IMAGERY OF A SAMPLE

(75) Inventor: David Levitz, Tel Aviv (IL)

(73) Assignee: MobileODT Ltd., Tel Aviv (IL)

(*) Notice: Subject to any disclaimer, the term of this patent is extended or adjusted under 35 U.S.C. 154(b) by 46 days.

(21) Appl. No.: 14/239,793

(22) PCT Filed: Aug. 21, 2012

(86) PCT No.: PCT/IB2012/054222
§ 371 (c)(1),
(2), (4) Date: Apr. 14, 2014

(87) PCT Pub. No.: WO2013/027173
PCT Pub. Date: Feb. 28, 2013

(65) Prior Publication Data
US 2014/0285812 A1 Sep. 25, 2014

Related U.S. Application Data

(60) Provisional application No. 61/525,783, filed on Aug. 21, 2011, provisional application No. 61/549,487, filed on Oct. 20, 2011.

(51) Int. Cl.
G01B 9/02 (2006.01)
A61B 5/00 (2006.01)
G01N 21/47 (2006.01)

(52) U.S. Cl.
CPC ........ *G01B 9/02091* (2013.01); *A61B 5/0066* (2013.01); *G01N 21/4795* (2013.01)

(58) Field of Classification Search
CPC ....... G01N 21/4795; G01N 2021/1787; G01N 21/3563; G01N 21/359; G01N 23/046;
(Continued)

(56) References Cited

U.S. PATENT DOCUMENTS 7,355,716 B2 * 4/2008 de Boer ............... A61B 5/0059
356/479
7,643,153 B2 * 1/2010 de Boer ............... A61B 5/0059
356/479
(Continued)

FOREIGN PATENT DOCUMENTS

GB 2231958 A 11/1990

OTHER PUBLICATIONS http://hyperphysics.phy-astr.gsu.edu/hbase/geoopt/lenseq.html.*
(Continued)

*Primary Examiner* — Tarifur Chowdhury
*Assistant Examiner* — Mohamed K Amara
(74) *Attorney, Agent, or Firm* — Roach Brown McCarthy & Gruber, P.C.; Kevin D. McCarthy

(57) ABSTRACT

A multi-modal imaging and optical property measurement device that is integrated into an interferometer. Data acquired by the multiple imaging modalities in parallel include measurements of single-scattered, multiple-scattered, and diffuse light that enable characterization of different ranges within different depth regions in the sample. The system includes different interferometer configurations and different imaging modalities, and has a signal-processing unit that associates and co-registers interferometric, multi-spectral, and polarization sensitive measurements to derive and analyze optical properties of a sample and enhance an image display of the sample.

20 Claims, 12 Drawing Sheets

(58) Field of Classification Search
CPC ..... A61B 3/102; A61B 3/1225; A61B 5/0066; A61B 5/0073; A61B 5/0059; A61B 6/032; A61B 2019/5234; A61B 8/483; A61B 2019/524; G01B 9/02091; G01B 2290/45; G01B 9/02004; G01B 9/02044; G01B 9/02058; G01B 9/02063; G01B 2290/70; G01B 9/02083; G01B 9/0203; G01B 9/02069; G01B 9/02007; G01B 9/02027; G01B 9/0209; G01B 9/02087; G01B 9/02057; G01B 9/0201; G01B 9/0205; G01B 2290/65; G01B 9/02089; G01B 11/2441; G01B 9/02072; G01B 9/02084
USPC ........................................................ 356/479
See application file for complete search history.

(56) References Cited

U.S. PATENT DOCUMENTS

| | | | | |
|---|---|---|---|---|
| 7,809,225 | B2* | 10/2010 | Bouma | G02B 6/02042 385/116 |
| 8,047,053 | B2* | 11/2011 | Call | G01N 1/2202 73/28.01 |
| 8,469,514 | B2* | 6/2013 | Utsunomiya | A61B 3/0058 351/206 |
| 9,033,499 | B2* | 5/2015 | Iwase | A61B 3/0025 351/206 |
| 9,115,972 | B2* | 8/2015 | Hirose | A61B 3/102 |
| 9,247,873 | B2* | 2/2016 | Iwase | G01B 9/02091 |
| 9,291,500 | B2* | 3/2016 | Robinson | G01J 3/0224 |
| 2003/0028100 | A1* | 2/2003 | Tearney | A61B 1/00165 600/431 |
| 2008/0024767 | A1 | 1/2008 | Seitz | |
| 2008/0230705 | A1* | 9/2008 | Rousso | A61B 5/415 250/363.04 |
| 2009/0021724 | A1* | 1/2009 | Mahadevan-Jansen | A61B 5/0066 356/73 |
| 2009/0270702 | A1* | 10/2009 | Zeng | A61B 5/0075 600/323 |
| 2009/0316160 | A1 | 12/2009 | Izatt et al. | |
| 2010/0166293 | A1 | 7/2010 | Sugita et al. | |
| 2011/0026010 | A1 | 2/2011 | Walker | |
| 2011/0112385 | A1* | 5/2011 | Aalders | A61B 5/0059 600/322 |
| 2015/0348287 | A1* | 12/2015 | Yi | G06T 11/003 382/131 |

OTHER PUBLICATIONS

"Atmospheric Propagation Effects Relevant to Optical Communications" to K. Shaik; TDA Progress Report (1988) pp. 180-200.*
"Absorption and scattering depth profile reconstruction in turbid media based on spectroscopy measurements" to Reif et al. (Biomed. App. of Light Scattering, 6446-2007).*
Determination of the optical properties of turbid media from a single Monte Carlo simulation, to Kienle et al. (Phys. Med. Biol., 41, (1996).*
Separation of absorption and scattering properties of turbid media using relative spectrally resolved cw radiance measurements, to Grabtchak et al., Biomed. Opt. Exp. 10, (2012).*
"Quantifying the absorption and reduced scattering coefficients of tissuelike turbid media over a broad spectral range with noncontact Fourier-transform hyperspectral imaging", to Pham et al. (Appl. Opt., 39—(2000)).*
Kienle et al. "Determination of the optical properties of turbid media from a single Monte Carlo simulation"; Phys. Med. Biol. 41 (1996) 2221-2227.*
Pham et al. "Quantifying the absorption and reduced scattering coefficients of tissuelike turbid media . . . "; 2000 vol. 39, No. 34 Applied Optics.*
Grabtchak et al. "Separation of absorption and scattering properties of turbid media using relative spectrally resolved cw radiance measurements"; 2012 / vol. 3, No. 10 / Biomedical Optics Express.*
Reif et al. "Absorption and scattering depth profile reconstruction in turbid media based on spectroscopy measurements"; Proc. of SPIE vol. 6446, 644605.1-7, (2007).*
Extended European Search Report dated Jun. 15, 2015, of European patent application No. 12825628.6; 8 pages.
Search Report of International Application No. PCT/IB2012/054222 dated Feb. 15, 2013.
https://www.thorlabs.com/newgrouppage9.cfm?objectgroup_id=2913, last viewed on Aug. 16, 2016. 1 page.

* cited by examiner

ASSOCIATING OPTICAL COHERENCE TOMOGRAPHY (OCT) DATA WITH VISUAL IMAGERY OF A SAMPLE

CROSS REFERENCE TO RELATED APPLICATIONS

This application is a National Phase Application of PCT International Application No. PCT/IB2012/054222, International Filing Date Aug. 21, 2012, entitled "ATTACHING OPTICAL COHERENCE TOMOGRAPHY SYSTEMS ONTO SMARTPHONES", published on Feb. 28, 2013 as International Publication Number WO/2013/027173, which claims the benefit of U.S. Provisional Patent Application No. 61/525,783 filed on Aug. 21, 2011 and of U.S. Provisional Patent Application No. 61/549,487 filed on Oct. 20, 2011, which are incorporated herein by reference in their entirety.

BACKGROUND

1. Technical Field

The present invention relates to the field of optical coherence tomography (OCT) systems, and more particularly, to an OCT system implementing multiple viewing and processing configurations.

2. Discussion of Related Art

FIG. 1A illustrates an Optical Coherence Tomography (OCT) system 50 according to prior art. OCT system 50 comprises a light source 90, e.g. a broadband (white) light source, which is used to generate a light beam. OCT system 50 further comprises a low-coherence interferometer 72 including e.g. a beam splitter 70 (as part of a Michelson interferometer), to split the light beam into a sample beam directed at a sample 80 and reflected therefrom, and a reference beam which may be directed at a mirror 85 and reflected therefrom. Interferometer 72 is arranged to receive the reflections of the sample beam and the reference beam, and create an interference pattern which is measured by a detector 95, such as a photodiode. Because of the source's wide spectral bandwidth, an interference pattern will emerge only if the pathlength between light reflected from the reference and sample arms are within the temporal coherence length of the source. A depth-scan (A-scan) can be formed under various configurations. A time domain OCT image physically scans the reference arm in the axial direction, thereby changing the delay and enabling probing different depths in the sample. A spectral domain OCT image keeps the reference arm position constant but replaces the detector with a spectrometer consisting of a dispersive element such as a prism for example, coupled to a detector line array such as a CCD camera. The A-scan is found from the inverse Fourier transform of the spectral interference pattern. Alternatively, the spectral interference pattern can also be attained while keeping the reference arm position fixed and while using a point detector by scanning (or "sweeping" or "tuning") the light source through narrow monochromatic bands. This OCT configuration requires synchronizing detector acquisition times with the instantaneous light source wavelength. In this configuration, known as swept source OCT, the A-scan is also determined from the inverse Fourier transform of the spectral interferogram. Creating a two-dimensional (2D) or three-dimensional (3D) OCT image requires scanning the beam on the sample. The scanning OCT configuration scans the beam between successive A-scans, while the full field OCT acquires from multiple lateral positions in parallel (i.e., an imaging configuration) using a one dimensional (1D) or 2D detector array.

The following documents illustrate aspects of the prior art. Zuluaga and Richards-Kortum 1999 ("Spatially resolved spectral interferometry for determination of subsurface structure", Optical letters 24:8 pages 519-521) disclose a two-dimensional non-scanning OCT system. U.S. patent application no. 2008/0158550 discloses a non-scanning OCT implementation in two dimensions, and Abdulhalim 2011 ("Non-display bio-optic applications of liquid crystals", Liquid crystals today 20:2 pages 44-66) discloses a multimodal OCT system implementing a liquid crystal devices to control beam characteristics.

BRIEF SUMMARY

One aspect of the present invention provides an optical coherence tomography (OCT) system comprising: a light source arranged to generate a light beam, an interferometer configured to generate from the light beam a sample beam aimed at a sample and a reference beam aimed at a reflecting surface such as a mirror, and to superimpose a sample reflection of the sample beam and a reference reflection of the reference beam to yield a measurement beam (interference pattern), an imaging unit comprising an OCT detector or detector array arranged to derive OCT data from the measurement beam, a viewing detector or detector array (including e.g. multi-spectral imaging and/or polarized light imaging) and a signal processing unit, and a beam splitter configured to project the sample reflection onto the viewing detector array to generate a sample image, wherein the signal processing unit is arranged to associate and co-register the OCT data with the sample image to yield a multi modal measurements of the sample.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION

Figure 1A:
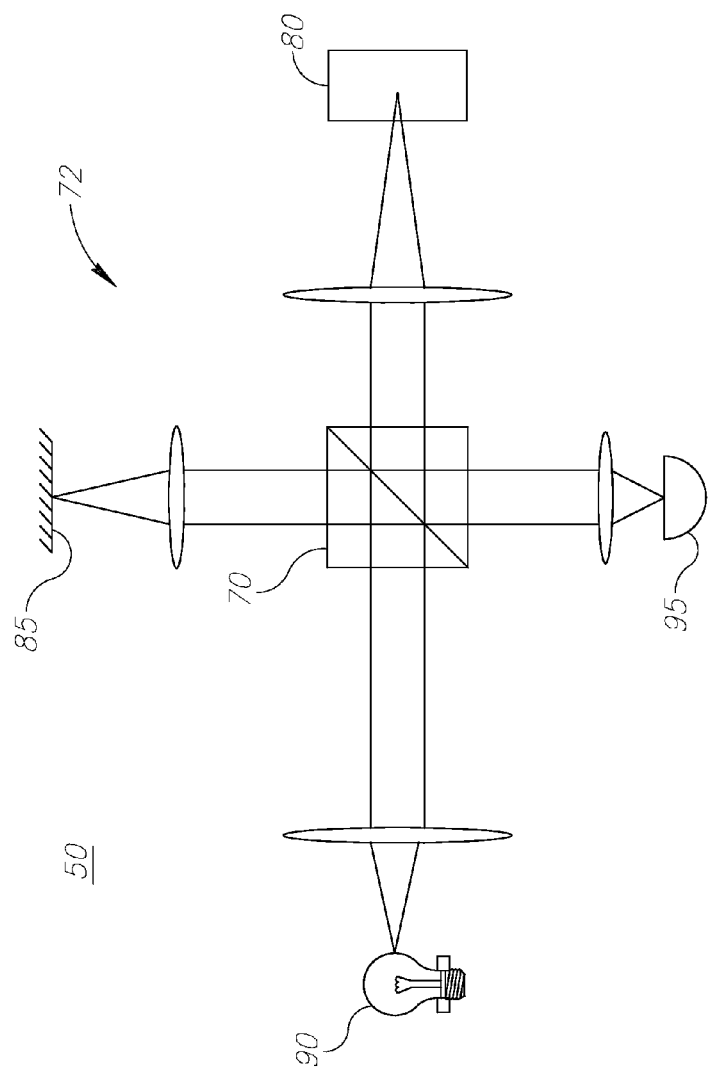
FIG. 1B is a schematic illustration of various measurement zones in a sample, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1A is an illustration of a prior art Optical Coherence Tomography (OCT) system;

The propagation of light in tissue is guided primarily by scattering and absorption. Light scattering can be quantified in terms of number and directionality, while absorption can only be quantified by number. The scattering coefficient $\mu_s$ is a measure of the number of scattering events. It is defined as the inverse of the mean distance between successive scattering events. Similarly, the absorption coefficient $\mu_s$ is defined as the inverse of the mean distance between successive absorption events. The scattering anisotropy g is a measure of the directionality of the scattered light, namely the mean cosine of energy scattered along polar angular direction.

Other tissue properties that affect light transport in tissue include the refractive index n, the tissue birefringence $\Delta n$, and the tissue Müller matrix M. Refractive index n describes how fast light travels in the medium relative to a vacuum. Birefringence $\Delta n$ describes the maximum difference in refractive index between the ordinary and extraordinary axes of a material. Birefringence depends on the polarization and the direction of propagation of the light in the sample. Müller matrix M describes how various polarizations of a field (as described by the Stokes vector) propagate through a material. It is a more complete descriptor of the polarization properties of a material than $\Delta n$.

Optical scattering in turbid media such as tissue can be divided into 3 regimes, based on the average number of times the light scattered, which is given by the dimensionless quantity the optical depth $\mu_s z$.

Figure 1B:
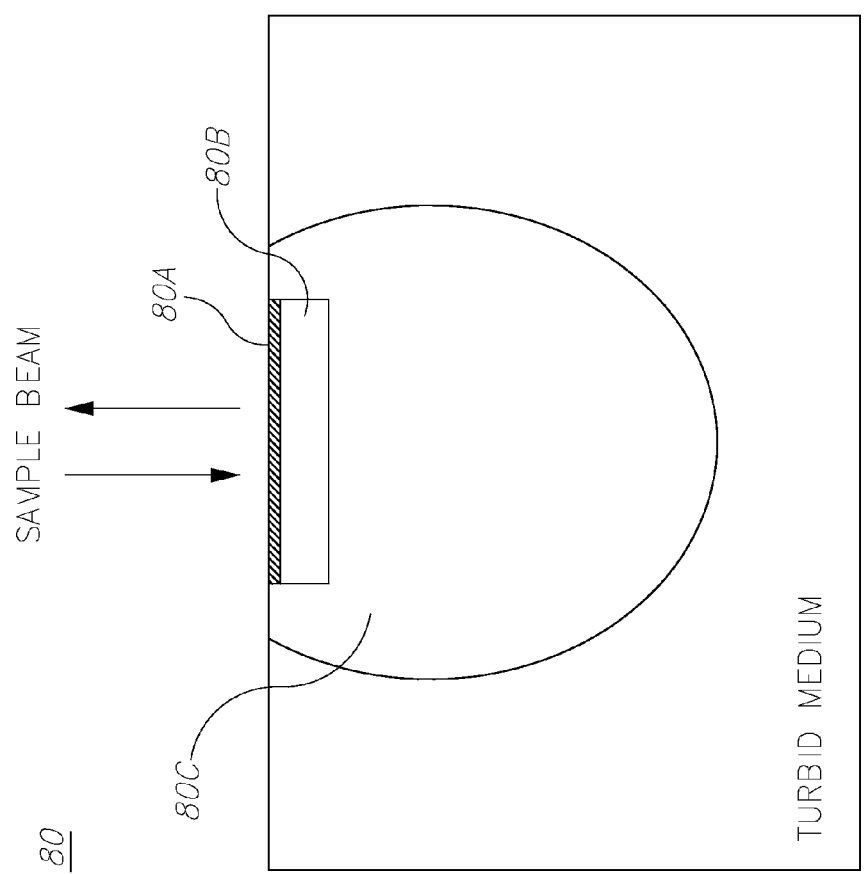

FIG. 1B is a schematic illustration of various measurement zones in sample 80, according to some embodiments of the invention. In respect to the surface of sample 80 onto which the sample beam is directed, an area 80A closest to the surface is the single scattering regime, which is measurable by, e.g., polarized light imaging to derive, e.g. the parameters $\mu_s$ (the scattering coefficient), $\Delta n$ (birefringence parameter) and M (the Müller matrix). An area 80B located deeper into sample 80B is the multiple scattering regime, which is measured by OCT or confocal laser-scanning microscopy (CLSM) to derive e.g. $\mu_s$ (the scattering coefficient) and g (the anisotropy factor of scattering). An area 80C which surrounds areas 80A and 80B is the light diffusion regime, which is measurable by, e.g. multi-spectral imaging to derive parameters such as $\mu_s'$ (a reduced scattering coefficient, equal to $\mu_s$ times (1−g)) and $\mu_a$ (the absorption coefficient). The presented system combines data from all three types of areas 80A, 80B, 80C to yield detailed multi-modal point measurements and/or imaging.

When the optical depth is less than one, light is said to be in the single scattering regime, i.e., it has on average undergone one scattering event or less. Single scattered light maintains basic properties like phase, polarization, and coherence. In imaging applications like CLSM and OCT, single-scattered light forms the sharp, well-defined structures in the image in the superficial part of the sample. In measuring optical properties of single-scattered light, it is generally accepted that one can fit one parameter, $\mu_s$.

When the optical depth is greater than 10, light is said to be in the diffusion regime, in which light propagation can be adequately approximated by the laws of diffusion, with energy moving from a high concentration (or fluence rate) to a lower concentration. Diffuse light has lost all its basic wave properties such as phase, coherence, and polarization, and in effect no longer acts as a wave. Diffuse light makes up most of the light detected by the human eye and in most photographic applications (including multi-spectral imaging), in which light entered a sample, scattered around, and exited the sample such that it was sensed by a detector or the eye. In measuring the optical properties of diffuse light, the parameters of interest that guide light transport in the tissue are $\mu_s'$ and $\mu_a$.

Light that has undergone on average between one and ten scattering events is said to be in the multiple-scattering regime. Here, the light has partially maintained its wave properties such that it can no longer simply be categorized as in either of the above scattering regimes. Multiple scattered light is found mostly in deep structures observed in OCT images and in some CLSM images. Multiple-scattered light allows making non-destructive measurements that separate $\mu_s$ and g, which is not possible using other methods.

There are several methods of measuring optical properties from tissue. In general, these methods consist of making experimental measurements and fitting the data to theoretical or numerical prediction using various analytical and computational methods.

Traditionally, the most common method for measuring optical properties is the integrating sphere, in which one measures the global flux of light that reflected from transmitted through a slab of tissue captured into a highly-reflective sphere coupled to a detector. A third (and difficult) measurement needed to determine all three optical scattering properties is the collimated transmission through the sample. The total diffuse reflectance and total diffuse transmission measurements are of light in the diffusion regime, while the collimated transmission is of light in the single scattering regime. The total diffuse reflectance, total diffuse transmittance, and collimated transmission measurements are then used in an algorithm (such as the inverse adding doubling algorithm), which indirectly yields back $\mu_s$, $\mu_a$, and g. An additional advantage is that integrating sphere is capable of making spectrally-sensitive measurements, giving a more complete description of the sample.

There are several drawbacks to the integrating sphere method. First and foremost, it requires a parallel thin slab of (explanted) tissue which is difficult to prepare and in effect means it is not possible to make in vivo measurements. Additionally, the measurements are corrupted by lateral scattering, in which light that scatters exits through the side of the slab and is mistaken for being absorbed. As a result, $\mu_a$ is overestimated by the inverse adding-doubling (IAD) algorithm, that is commonly used for this estimation. Given the drawbacks of non-trivial tissue preparation, overestimation of $\mu_a$, and general difficulty in the collimated transmission measurement, the integrating sphere method is not deemed an optimal method for measuring optical properties.

However, no method is capable of measuring all three optical scattering properties ($\mu_s$, $\mu_a$, and g) simultaneously and non-destructively, that is, without any tissue processing or modification. This is because every other method operates in one scattering regime or another, but not in all of them. The present invention operates in all three scattering regimes.

FIGS. 2A-2D are high level schematic illustrations of a multi modal OCT system 100, according to some embodiments of the invention. OCT system 100 incorporates a viewing detector 130 to allow additional processing and reference to the OCT image. Viewing detector 130 provides additional visual data about sample 80 that allows for measuring optical properties and enhancing the OCT data. OCT system 100 hence improves prior art OCT systems 50 by providing multi-modal information about sample 80.

Figure 2A:
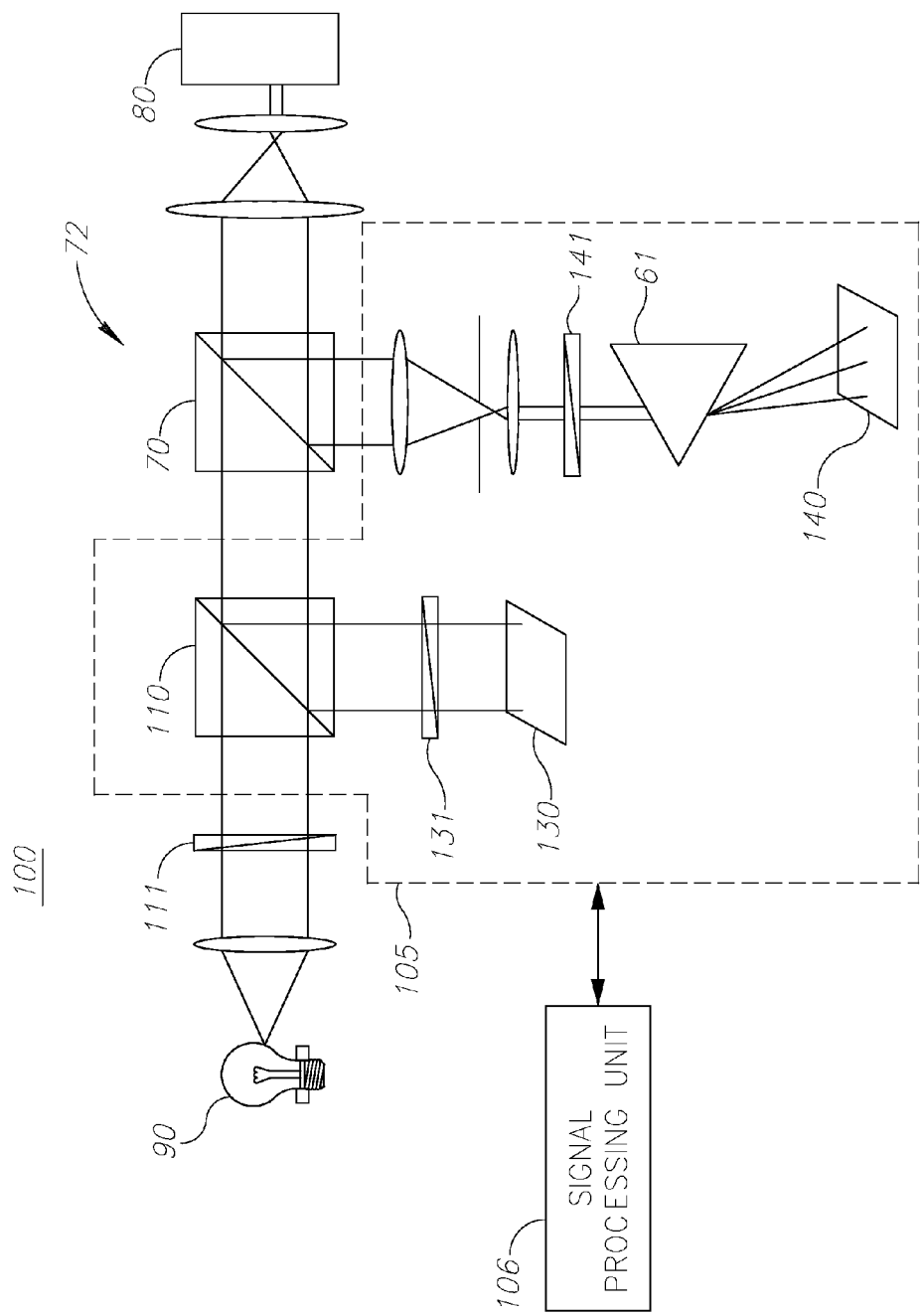
FIGS. 2A-2D are high level schematic illustrations of an OCT system, according to some embodiments of the invention.

As illustrated in FIG. 2A, Optical Coherence Tomography (OCT) system 100 comprises light source 90 arranged to generate a light beam (appropriate for implementing low coherence interferometry, e.g. collimated and/or diffused by diffusers and filtered, e.g. to have well defined polarization), interferometer 72 (comprising e.g. a beam splitter 70) configured to generate from the light beam a sample beam aimed at sample 80 and reference beam, and to superimpose a sample reflection of the sample beam and a reference reflection of the reference beam to yield a measurement beam, an imaging unit 105 comprising an OCT detector 140 arranged to derive OCT data from the measurement beam, viewing detector 130 and a signal processing unit 106, and a beam splitter 110 configured to project the sample reflection through a filter 131 onto viewing detector 130 to generate a sample image. The sample beam that is aimed at sample 80 may be collimated such that it images in scatter-mode. Signal processing unit 106 is arranged to associate and co-register the OCT data with the sample image to yield multi modal measurements or imaging of sample 80, for example, signal processing unit 106 may generate a combined, co-registered image of OCT data and multi-spectral data. The multi modal image of sample 80 may comprise point measurements, line measurements, area measurements, or volume measurements as well as images of sample 80 in two or three dimensions, using a range of configuration possibilities described below. For example, imaging system 100 may produce a three dimensional image of sample 80 that comprises multispectral data, polarization data and OCT data. Light source 90 may comprise a combination of sources with various wavelength ranges and polarization modes for different modalities, as well as diffusers to homogenize the beams' irradiance. System 100 may be arranged to allow acquiring images of adjacent areas of sample 80 and tiling them together into the sample image, i.e. to generate a mosaic image of sample 80. System 100 yields multi modal images in a non-destructive, non-invasive manner.

Viewing detector 130 and OCT detector 140 may be point detectors, line detectors or detector arrays, and may incorporate scanning and/or parallel multi-element detection (images). In the following, viewing detector 130 is referred to as a viewing detector array 130 and OCT detector 140 is referred to as an OCT detector array 140 for the sake of simplicity, and without limiting the scope of the invention.

In embodiments, a cross-polarizer may be added in front of viewing detector 130 in order to filter out single-scattered light.

Optical elements such as lenses, mirrors, slits/pinholes, and spatial filters/spatial light modulators may be positioned in appropriate positions to control the light beams. For example, lens may include a compound lenses complex such as a microscope objective. Filters may be used to control the wavelength range, polarization, phase front of the beams, e.g. filter 111 controls the wavelength range and phase front of the light beam, filters 131 and 141 control properties (such as the polarization) received by viewing detector arrays 130 (for use as part of another imaging modality) and detector 140 (FIG. 2A) for OCT. Filters 111 and, 131, and 141 may also be used to correct for imaging aberrations or increase the signal to noise ratio of the various imaging modalities. A dispersive element 61 may be used to produce a separation of the interference pattern into wavelength ranges. In embodiments, optical elements may comprise optical coatings (high reflection and/or anti-reflection) to bring about a unidirectional light propagation, according to a specific optical planning of system 100.

The term "polarizer" or "polarizing filter" is defined in the present application as an optical element which influences the polarization of a light beam that passes therethrough. Examples include linear and circular polarizers of various types that are known in the art.

FIG. 2A further illustrates a common path configuration, in which the reference beam follows the same optical path as the sample beam and a reflective surface in the sample arm serves as the reference.

In embodiments, OCT system 100 may comprise viewing detector array 130 and/or OCT detector array 140 that is arranged to measure optical scattering parameters of sample 80, to enhance the OCT data. For example, an OCT signal can be modeled as $R = \rho \exp(-\mu z)$ with $\rho$ being the reflectivity given by $\mu_s\, b(g)\, \Delta z$, $\mu$ being the attenuation given by $2G(\mu_s\, a(g) + \mu_a)$, optical properties such as the scattering coefficient $\mu_s$ (indirectly) measuring particle density, anisotropy factor g (indirectly) measuring particle sizes, or absorption coefficient $\mu_a$ may be measured to enhance the generated images, G is a geometrical factor caused by the numerical aperture of the objective lens, a(g) is a numerical factor describing how g affect focusing in a turbid medium, and b(g) represents the fraction of backscattered light collected by the objective lens. More details regarding these measurements are presented below. Other models for measuring optical scattering parameters include the single scattering model and the extended Huygens-Fresnel model.

Many methods that measure optical properties are based on diffuse reflectance from the sample. Because such methods are based on diffuse light in which the light has traversed long pathlengths, it is not possible to separate $\mu_s$ and g, which are instead observed as the lumped parameter $\mu_s'$ (reduced scattering coefficient). However, the long pathlengths do enable measuring $\mu_a$, which is typically much smaller than $\mu_s$ and cannot be detected without long pathlength measurements.

One common way to make diffuse reflectance measurements involves point illumination and point detection, measured at a distance r from the source. The optical properties of the tissue determine how the light will propagate and how much will exit at various r values. Thus, by measuring the light that escapes as a function of source-detector separation r (also known as R(r) measurements) one can create a dataset that is fit to a theoretical model. The most accepted analytical equation for the spatially resolved diffuse reflectance from point illumination was solved by Farrell, Patterson, and Wilson in 1992 ("A diffusion theory model of spatially resolved, steady-state diffuse reflectance for the noninvasive determination of tissue optical properties in vivo", Medical Physics 19(4), 879-888). This model assumes the light can be modeled as if it diffused from a point source located one mean-free-path (mfp) below the sample surface. To account for the tissue surface, the boundary condition imposed assumes a negative point source located at 7 mfp above the sample surface. And although this model is based on point-illumination and point-detection, it is possible to convolve the expression for arbitrarily shaped sources and detectors.

In addition to spatially resolved diffuse reflectance measurements, an alternative method to measure the diffuse optical properties of the tissue involves modulating the illumination either in space or time. Spatial modulation (for example using spatial pattern illumination) can be used to measure the optical properties as part of an optical tomography setup, as the amount of light reaching a detector depends on the illumination and optical properties of the tissue. Using spatial patterning may improve the visualization of sample 80 through viewing detector 130 or OCT detector 140.

Temporal modulation (for example using a chopper or pulsed light source) creates a modulated diffusion pattern that propagate through the sample in what is also known as photon density waves. The amplitude and phase of these photon density waves (relative to those of the illumination) diffuse through the sample and contain information about its optical properties. Thus, a spatial or temporal frequency sweep of illumination creates a dataset from which it is possible to determine the optical properties.

Diffusion theory fails near sources, detectors, and boundaries. Such conditions can also occur if the source-detector separation is small, and the light collected did not scatter much before escaping the sample. In such cases, one can numerically model the light propagation in the tissue using methods such as Monte Carlo (MC) simulations, a common method for modeling stochastic events such as scattering step sizes and directionality. MC models light as power transport, dividing the light into "photons" (small energy particles) and using a random number generator to determine how such photons propagate (e.g. scatter and absorb) in the medium. The most common stochastic events modeled in MC programs (such as MCML as presented by Wang, Jacques and Zheng in 1995 ("MCML—Monte Carlo modeling of light transport in multi-layered tissues", Computer methods and programs biomedicine 47(2) 131-146) are the distance between scattering events and the new photon trajectory. Because of its inherent flexibility in controlling sample geometry, illumination/collection, etc., MC methods have replaced many analytical models of light propagation in tissue.

In certain embodiments of the present invention, Monte Carlo-based methods may be used to determine optical properties. In such cases, the source-detector separation is (at least in part) small. An example is wide field illumination and a camera imaging configuration. Here, the broad illumination beam can be subdivided into a 2D array of infinitesimal "pencil beams" Relative to the detection array pixels (the area covered by the camera), some of the illumination pencil beams are sufficiently far such the collected light is diffuse, while others are not. Such cases where even part of the optical geometry contains small source-detector separations, require MC modeling and inverse MC analysis.

Inverse MC analysis involves running forward MC simulations to map out how experimental output data will vary with respect to several variables. This mapping can be done several ways. One such mapping method is numeric, that is, creating a grid that connects input and output parameter values and interpolating experimental results within the context of the grid. An alternative way to do the mapping is analytically, by describing the output data as a function of the input parameters using analytical regressions. What is common to both methods is the use of forward simulations to solve the inverse problem. Inverse MC analysis has been used, among other things, to measure optical properties ($\mu_s'$, $\mu_a$) in diffuse reflectance (and transmittance) measurements, as well as to measure optical properties ($\mu_s$, g) from depth scans in OCT and CLSM data.

Figure 2B:
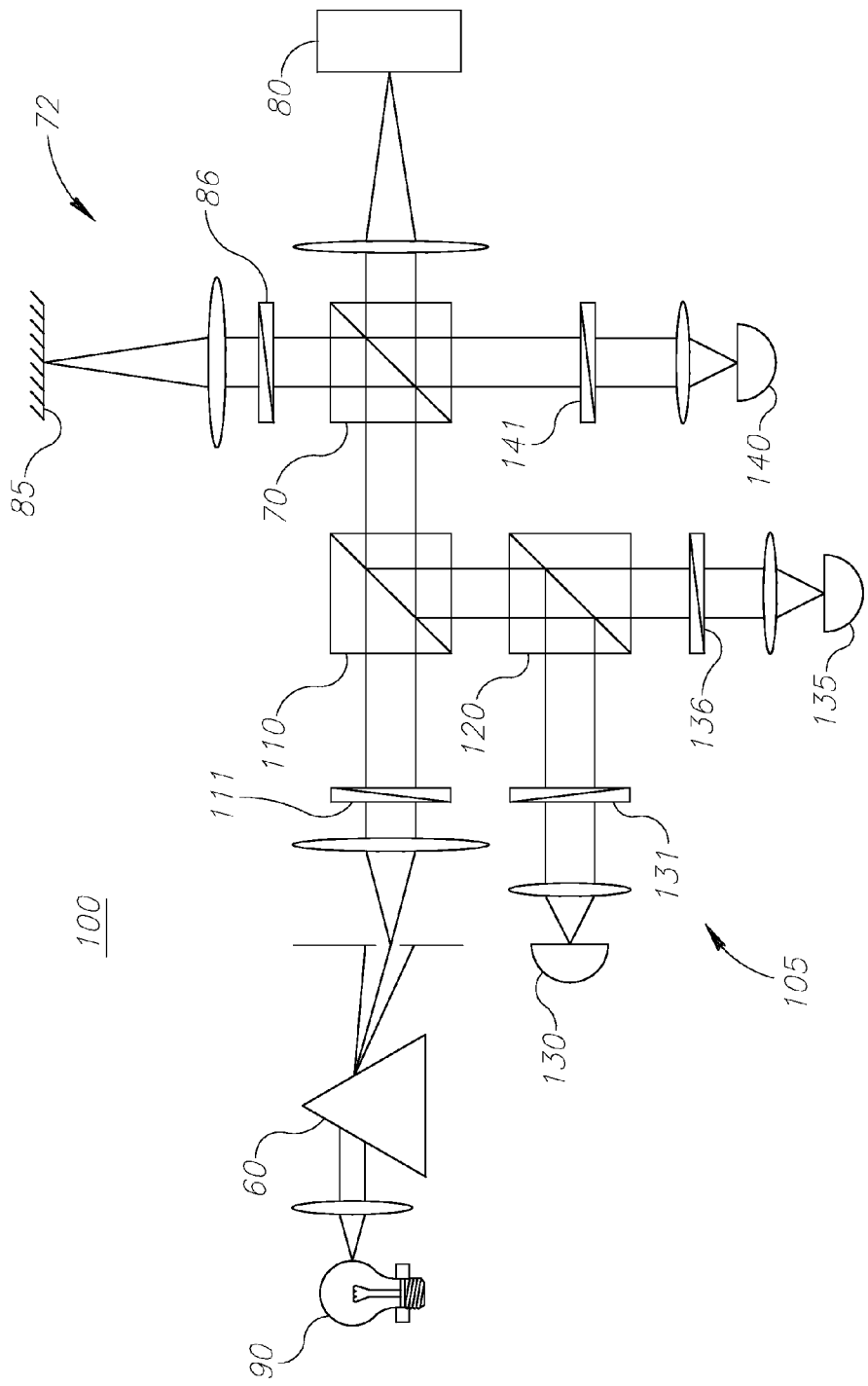

As illustrated in FIG. 2B, OCT system 100 may comprise a viewing beam splitter 120 that separates the sample reflection that did not interfere with the OCT reference into at least two beams that are passed through different filters 131, 136 and detected by at least two corresponding viewing detectors 130, 135, to compare the filtered parameters of the sample reflection. Filters 131, 136 may be selected to enhance specified features of the sample image and allow further processing thereof.

FIG. 2B further illustrates using a dispersive element 60 to sweep a wavelength range to produce a sequence of monochromatic light beams. The sequence may be used by signal processing unit 106 to extract depth information about sample 80, as interference patterns resulting from light beams of different wavelength yield information about different sample layers at different depths in the sample. In this way a three dimensional OCT imaging may be generated from a 2D sensor array (or two-dimensional images from a 1D array). Sweeping may be carried out in respect to time domain or frequency domain, and may be implemented in the light beam or in the reference beam (e.g. a filter 86 as a phase modulator in the reference arm to provide a delay instead of physical scanning, in an OCT configuration that may be used for phase-shifting interferometry measurements).

Figure 2C:
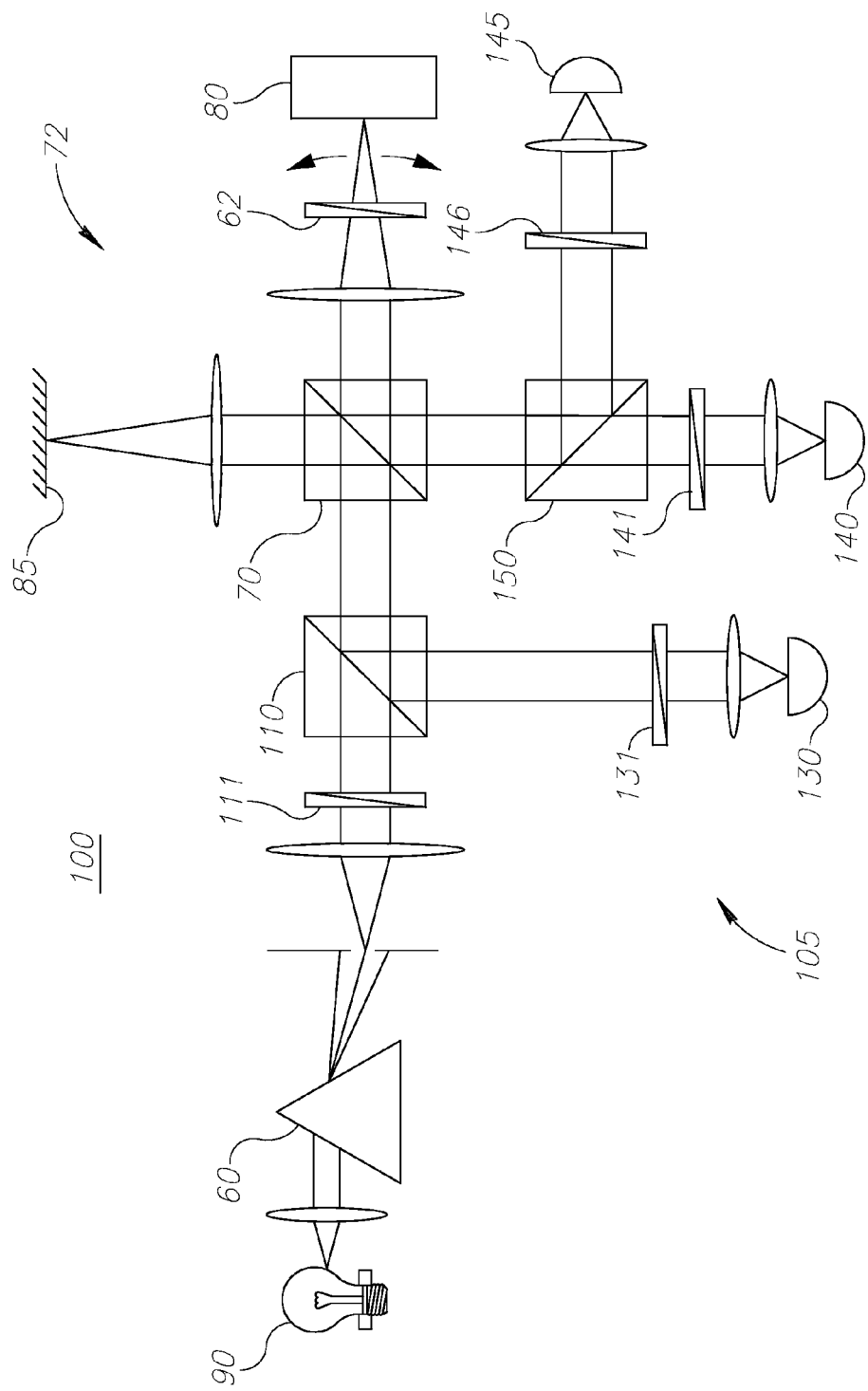

As illustrated in FIG. 2C, OCT system 100 may comprise a scanning filter 62 arranged to scan sample 80 with sample beam. Additionally, OCT system 100 may comprise measurement beam splitter 150 that splits the measurement beam into at least two beams that are past through different filters 141, 146 and detected by at least two corresponding OCT detector arrays 140, 145, to compare the filtered parameters of the interference pattern. Filters 141, 146 may be selected to enhance specified features of the interference pattern and allow further processing thereof, such as polarization-sensitive OCT.

Figure 2D:
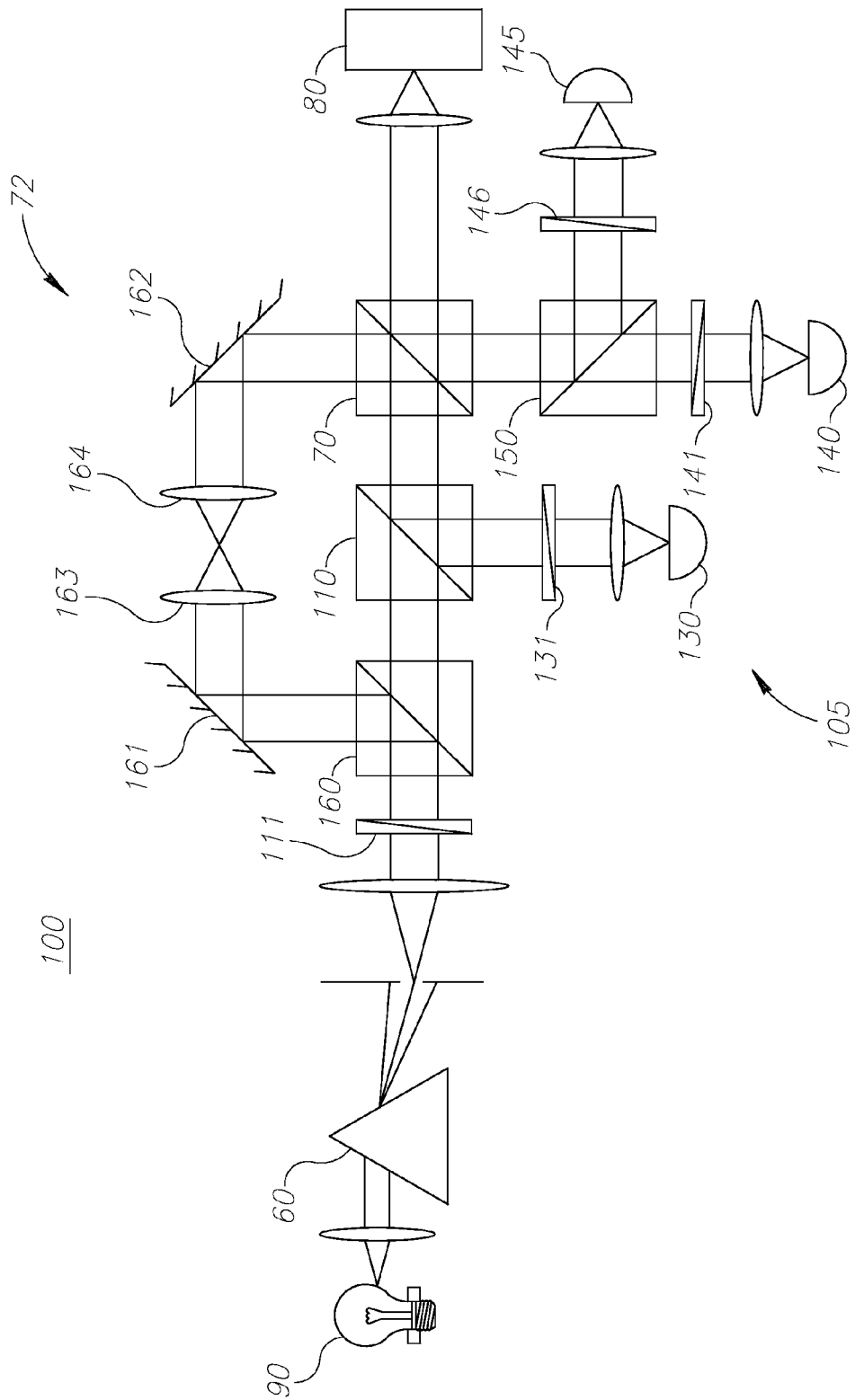

As illustrated in FIG. 2D, interferometer 72 may be configured as a Mach-Zehnder interferometer using as the reference beam light split from the light beam by a beam splitter 160. Light from beam splitter 160 may then pass over two mirrors 161, 162 and lenses 163, 164 to serve as the reflected reference beam entering beam splitter 70. Lenses between mirrors 161 and 162 are used for pathlength and group velocity dispersion compensation.

FIGS. 2B-2D further illustrate using single or multiple detectors, possibly with filter set combinations that enable multi-spectral imaging, polarized light imaging, fluorescence imaging, etc., placed just after the illumination and just before the detectors (viewing detector 130 and/or OCT detector 140). Such a configuration allows further sample data and OCT data to be derived from the sample beam and measurement beam respectively, by signal processing unit 106. For example, using polarization filters allows for measuring polarization properties (i.e. the birefringence) and may allow for additional analyses of single-scattered light. Phase retardance between different light beams going through a birefringent sample may be measured using polarization sensitive OCT or other forms of polarized light imaging enabled by the invention.

Because most imaging modalities are based on diffuse light, there are not many optical measurements that can clearly separate $\mu_s$ and g. The scattering anisotropy's effect can be mainly felt in the multiple-scattering regime, and so one must use methods that collect such light, namely either low coherence interferometry (and OCT) or CLSM. Here, one needs to look at the depth profile of the reflected light found in a single A-scan, and fit this A-scan to a theoretical model, as presented by Levitz, Hinds, Choudhury, Tran, Hanson, and Jacques in 2010 ("Quantitative characterization of developing collagen gels using optical coherence tomography", Journal of biomedical optics 15(2), 026019). The theoretical model relates the sample optical properties to the measured signal for a specified system configuration (illumination/detection). Several such theoretical models exist, based on various approximations (i.e., extended Huygens-Fresnel or the small-angle approximation to the radiation transport equation) or methods (i.e., inverse Monte Carlo).

In contrast to diffuse light measurements in which the light can penetrate centimeters into tissue with no lateral boundary, in LCI/OCT data (LCI is short for Low coherence interferometry), the optical properties of the sample are measured over a specified volume. That is, the A-scan (or a representative A-scan for a specified region) is truncated both laterally and axially. Moreover, each pixel in the A-scan represents a unique measurement of optical properties, and collectively the representative A-scan is a dataset that can be fit to a theoretical model. The coherence gating (and confocal gating) restricts the light that contributes to the signal based on space and time. Because the light is not yet diffuse, the effects of anisotropy and scattering coefficient on signal features such as attenuation and reflectivity are distinct and can therefore be separated.

Measuring optical properties using OCT requires taking note of various system parameters. For example, an OCT signal can only arise if the pathlengths between the two interferometer arms are perfectly matched to within microns of one another (e.g., within less than the temporal coherence length of the source). To maintain axial resolution (a factor in the various theoretical models used to measure optical properties), group velocity dispersion needs to also be matched. Additionally, to generate an interference pattern, the polarization of the two arms needs to be matched. In time-domain OCT systems (in which the reference arm pathlength is varied with time), the signal measured at the detector must be electronically filtered, demodulated and squared, in order to arrive at the intensity value that is known as the OCT signal. In spectral domain OCT systems (in which the reference arm is stationary and the point-detector is replaced with a dispersive element and a linear detector array), the spectral interferogram is converted into the time-delay interferogram using the inverse Fourier transform, after which the signal is demodulated and squared. The same holds true for swept source OCT, in which the illumination (and hence detection) is tuned over time but a point detector is used. Note that both spectral domain and swept source OCT data have a mirror image artifact and a DC artifact, both of which need to be removed prior to measuring the optical properties from the data.

There are a couple of methods to measure and characterize single-scattered light. The most common method involves fitting the superficial signal of an A-scan in OCT/CLSM to the single-scattering model, in which the signal follows an exponential decay with depth z, such that $I=\exp(-2\mu_s z)$. Note that this relation ignores defocusing effects. However, this method is not optimal for characterizing single-scattered light because of several reasons. One is that there is a vague restriction on what is the maximum optical depth ($\mu_s z$) for which the single-scattering model is no longer an adequate estimator of the light propagation. Moreover, one needs to fit the data in order to determine which pixels fall within the depth range of the model, and thus the measured properties of the tissue depend on how the measurement was made.

An alternative way uses the polarized nature of light. Earlier work by Jacques, Ramella-Roman and Lee in 2002 ("Imaging skin pathology with polarized light" Journal of Biomedical Optics, 7(3), 329-340) has shown that single-scattered light retains most of its polarization. If one were to image tissue using linearly polarized light, and implement polarization-sensitive detection that separately detects light polarized parallel (PAR) and perpendicular (PER) to the input polarization, it is possible to approximate the signal of the two polarizations as PAR=single-scattered+(½) diffuse light and PER=(½) diffuse light, in which PAR and PER represents the polarizations parallel and perpendicular to the illumination polarization. The single-scattered light can then be determined from the difference in the two polarization signals.

Although the initial work was done in standard bright field imaging (or microscopy), single-scattered light retains its polarization even in the added constraints of confocal and coherence gating. Thus polarization-sensitive detection for coherence- or confocal-gated light can be used to determine the single-scattering component of the light.

In general, an optical measurement M in turbid media can be thought of consisting of four components: a source function S, a transport function T (which depends on the optical properties), a collection geometry G, and a detector function D, such that M=STGD.

A similar measurement on a standard sample with known optical properties, $M_{std}$, can be described by $M_{std}=ST_{std}G_{std}D$. Within the context of the invention, the transport functions T and $T_{std}$ are basically reflectance values which can be characterized experimentally, and various standards with uniform reflectance (such as spectralon) already exist. Moreover, because the source and detector functions are constant across various measurements, a ratio of the two measurements leaves the transport, and a scaling constant GG, which $M/M_{std}=(T/R_{std})*(G/G_{std})=GG*T/R_{std}$, in which GG represents a lumped parameter equal to $(G/G_{std})$. Consequently, the ratio of two measurements, one on a test sample to one on a known reference, enables characterizing the sample using a model that describes light propagation in the sample for the measurement of interest. Note that the equation is valid for both diffuse measurements and multiple-scattering measurements. In measuring optical properties, it is imperative to select the correct expression for T, as this determines the accuracy of the measurements. There are several models for both diffusion and multiple-scattering regimes that could be used.

Figure 3:
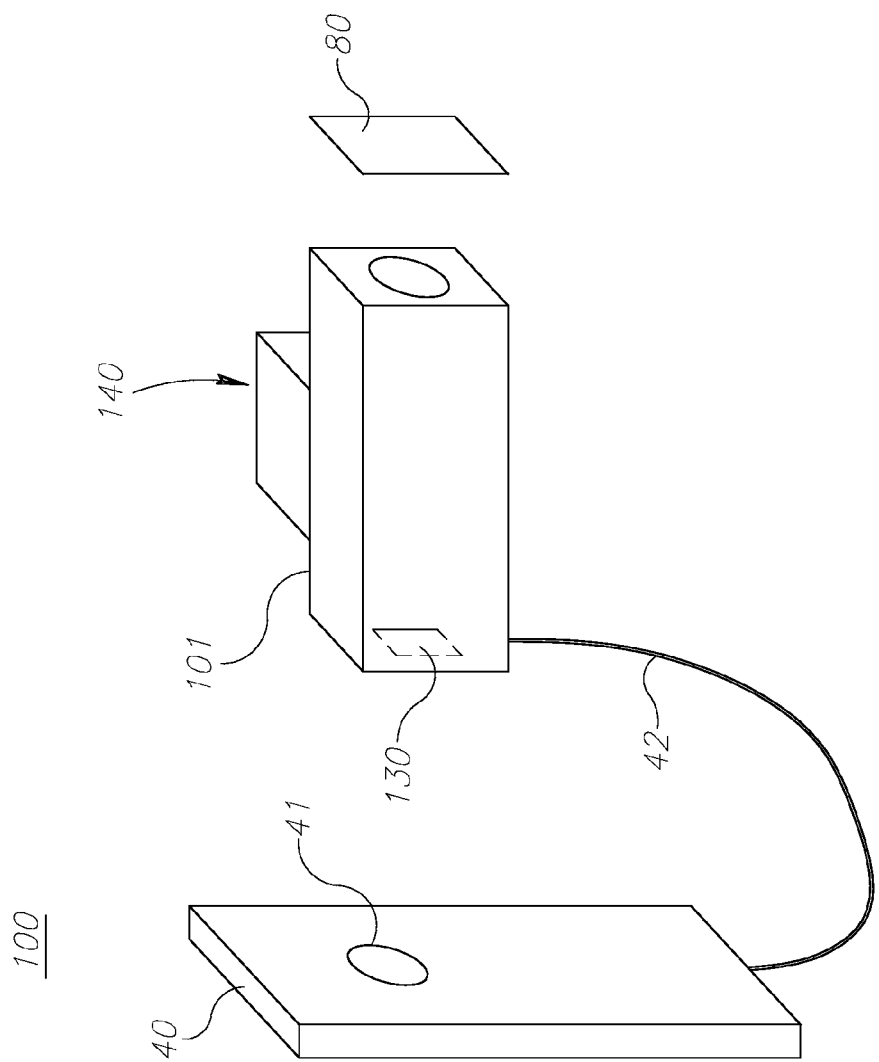
FIG. 3 is a high level schematic illustration of the OCT system associated with a computing device, according to some embodiments of the invention.

FIG. 3 is a high level schematic illustration of OCT system 100 associated with a computing device 40 such as a smartphone or a tablet computer, according to some embodiments of the invention. For example, light source 90, interferometer 72 and OCT detector array 140 may be encased in a housing 101 that is operably attachable to computing device 40, and signal processing unit 106 may be implemented in computing device 40. Viewing detector array 130 may either be an independent detector array, or may be a camera 41 of computing device 40. The operable attachment of housing 101 to computing device 40 may be carried out by physical contact or attachment, or by tethering housing 101 to computing device 40 (by a wire 42 or wireless). In embodiments, and signal processing unit 106 may be implemented in a cloud server.

Figure 4A:
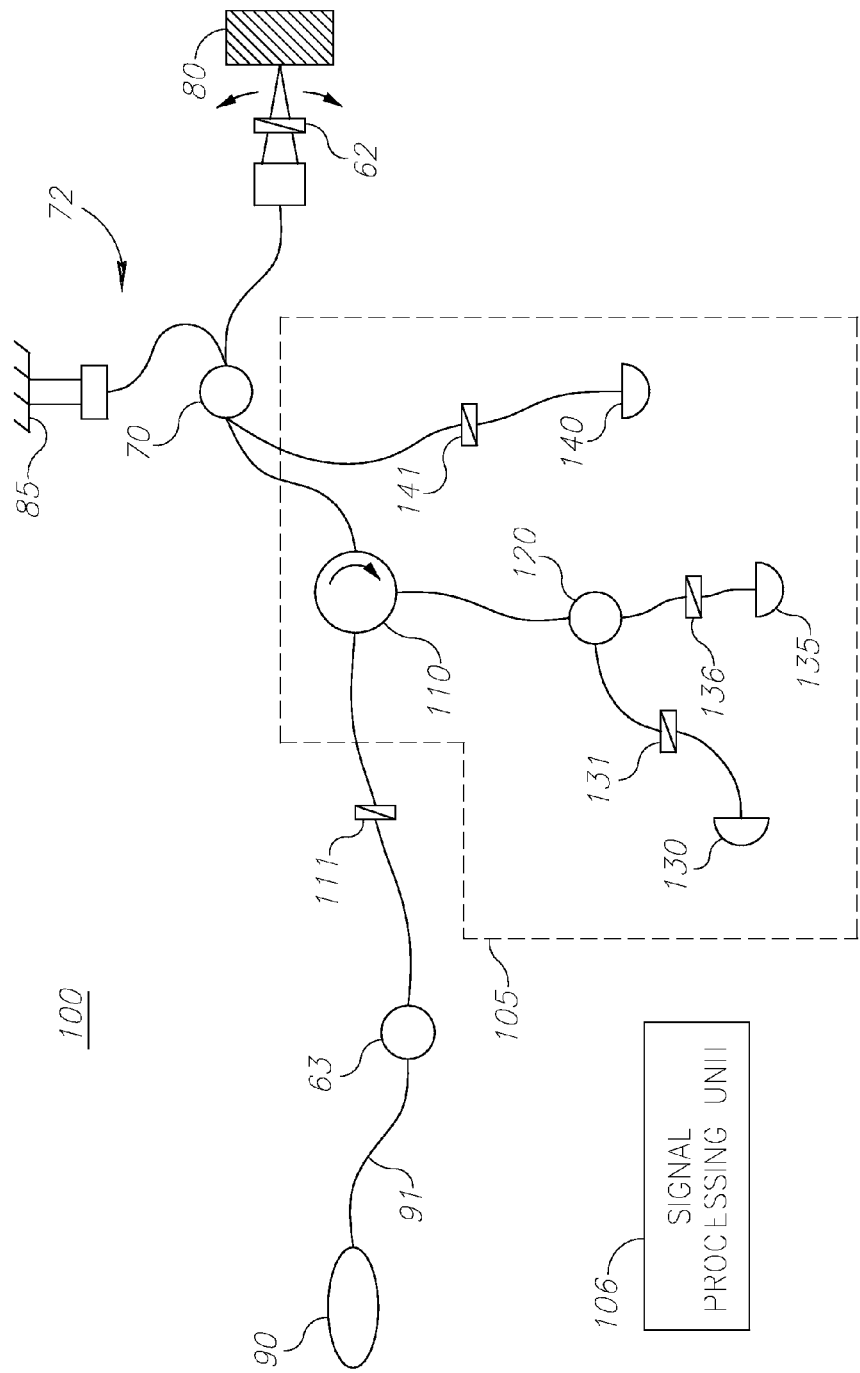
FIGS. 4A-4C are high level schematic illustrations of the OCT system implemented with fiber optics, according to some embodiments of the invention.
Figure 4B:
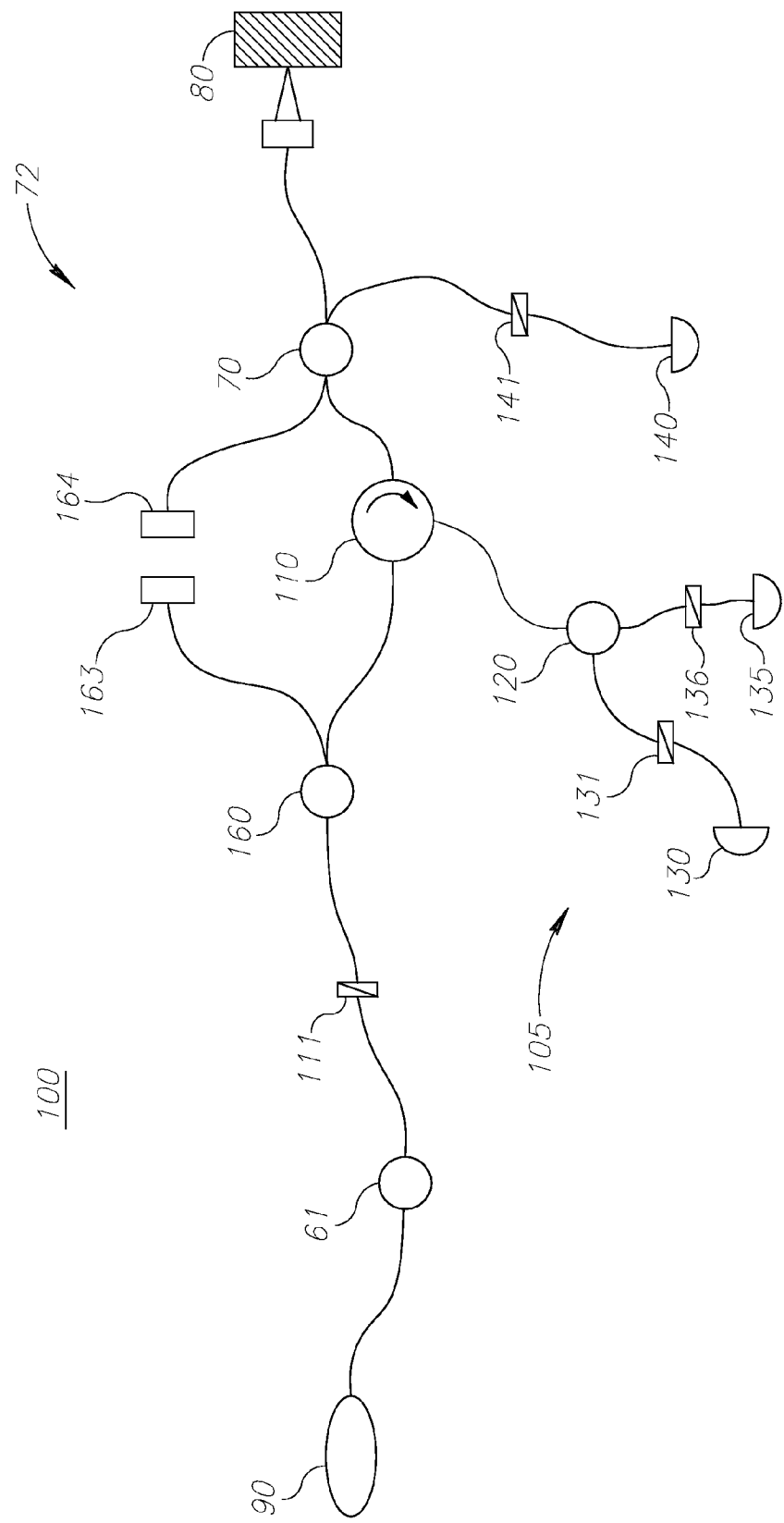
Figure 4C:
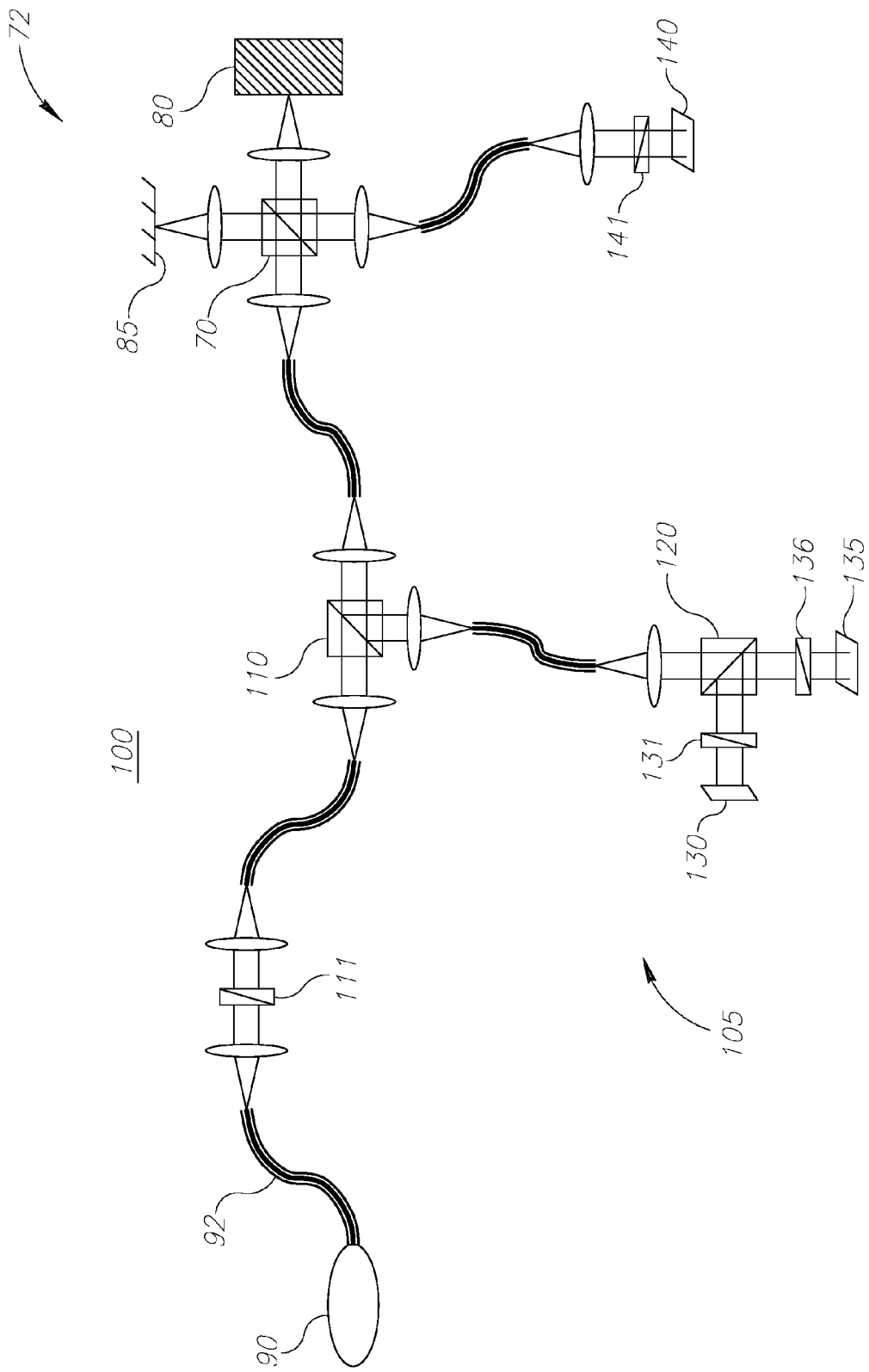

FIGS. 4A-4C are high level schematic illustrations of OCT system 100 implemented with fiber optics, according to some embodiments of the invention. FIG. 4A illustrates OCT system 100 implemented with optical fibers 91 that guide the various beams between the optical elements and to and from sample 80, mirror 85 and detectors 130, 135, 140. All optical elements illustrated in FIGS. 2A-2D may be implemented by corresponding elements that are coupled with optical fibers 91. For example, FIG. 4A is roughly analogous to FIG. 2B, and further exhibiting a fiber polarizer 63 for polarizing the light beam and allowing polarization measurements of sample beam and measurement beam, and a scanning filter 62 arranged to scan sample 80 with sample beam. In another example, FIG. 4B illustrates an implementation of a Mach-Zehnder interferometer, with beam splitter 160 and lenses 163, 164, which may be needed for dispersion matching. Light source 90 may comprise a tunable light source.

FIG. 4C illustrates OCT system 100 implemented with optical fiber bundles 92 that guide multiple beams of each kind and thus allow measuring OCT data in multiple lateral positions in parallel as part of an imaging setup, analogous to full-field OCT. The optical elements are selected correspondingly, for example, FIG. 4C us roughly analogous to FIG. 2B. Optical fibers 91 and optical fiber bundles 92 may be selected to maintain polarization.

The light beam may be configured to excite fluorescent pigments in sample 85, and viewing detector array 130 may be arranged to detect the fluorescence. Signal processing unit 106 may then be configured to locate directly the fluorescent pigments in the multi-spectral data, and present a corresponding combined image. In case of pixilated array detector in which sub-pixels are sensitive to different wavelength ranges (e.g., an RGB camera), the sub-pixels at higher wavelengths may be arranged to measure the fluorescence data.

In embodiments, the light beam may be patterned, and the pattern may be used to or improve the data in the various imaging modalities. The light beam may be temporally modulated to utilize the temporal data for improving the signal to noise ratio of the measurements by, e.g., allowing for electronic filtering of the detected signal in the various imaging modalities, as well as enable measuring optical properties.

In embodiments, the invention may be implemented to acquire point, one-dimensional, or 2-dimensional measurements, and combine them according to given algorithms. The invention may thus be implemented in a scanning or non-scanning configuration.

Clearly, OCT system 100 may be constructed to incorporate elements from different figures, for example, a fiber bundle implementation with split measurement beam and a Mach-Zehnder interferometer, an optical fiber implementation with split measurement beam, an optical fiber implementation with common path OCT and dispersive element 60, etc.

Figure 5A:
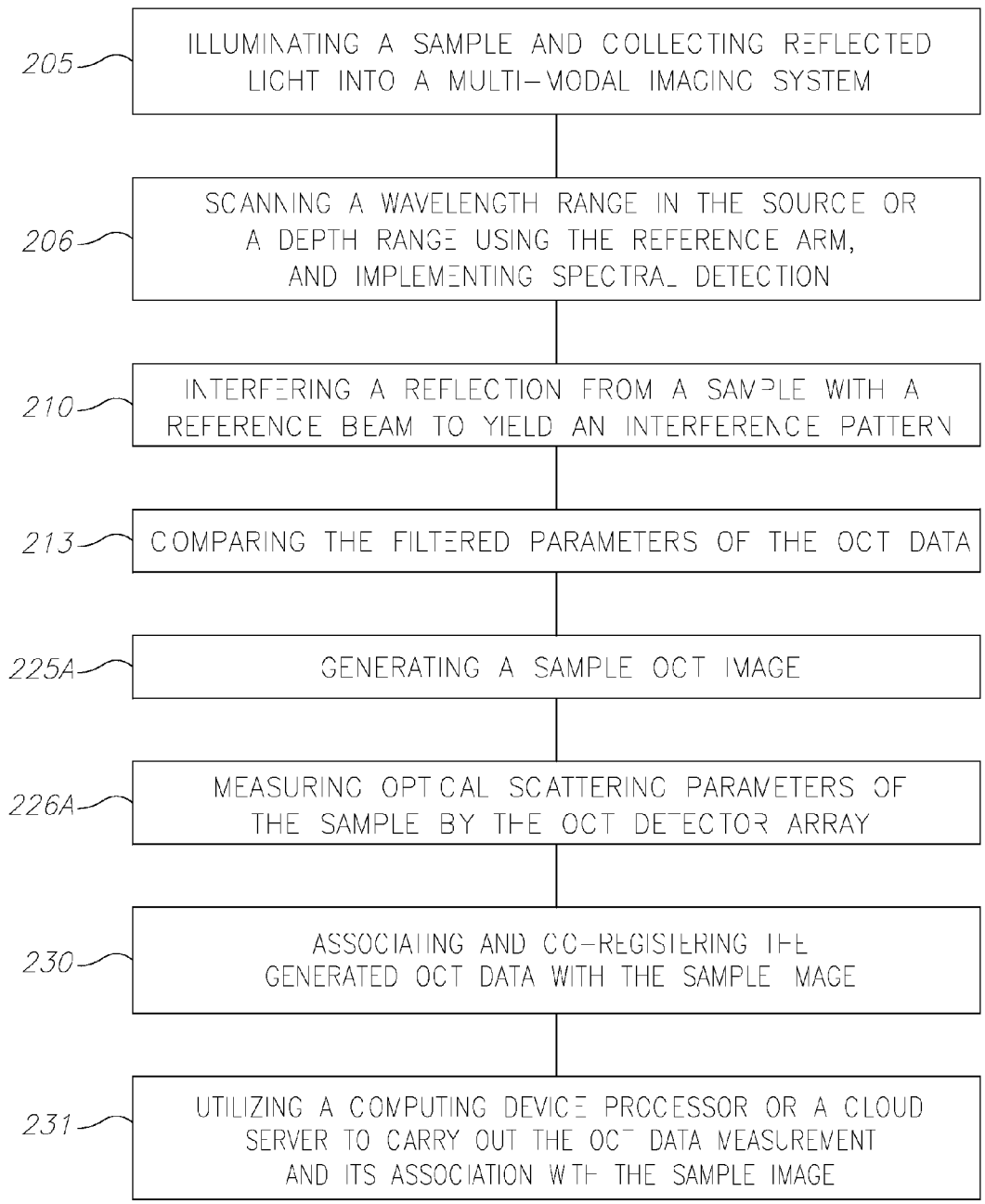
FIGS. 5A and 5B are high level schematic flowcharts illustrating an OCT method, according to some embodiments of the invention.
Figure 5B:
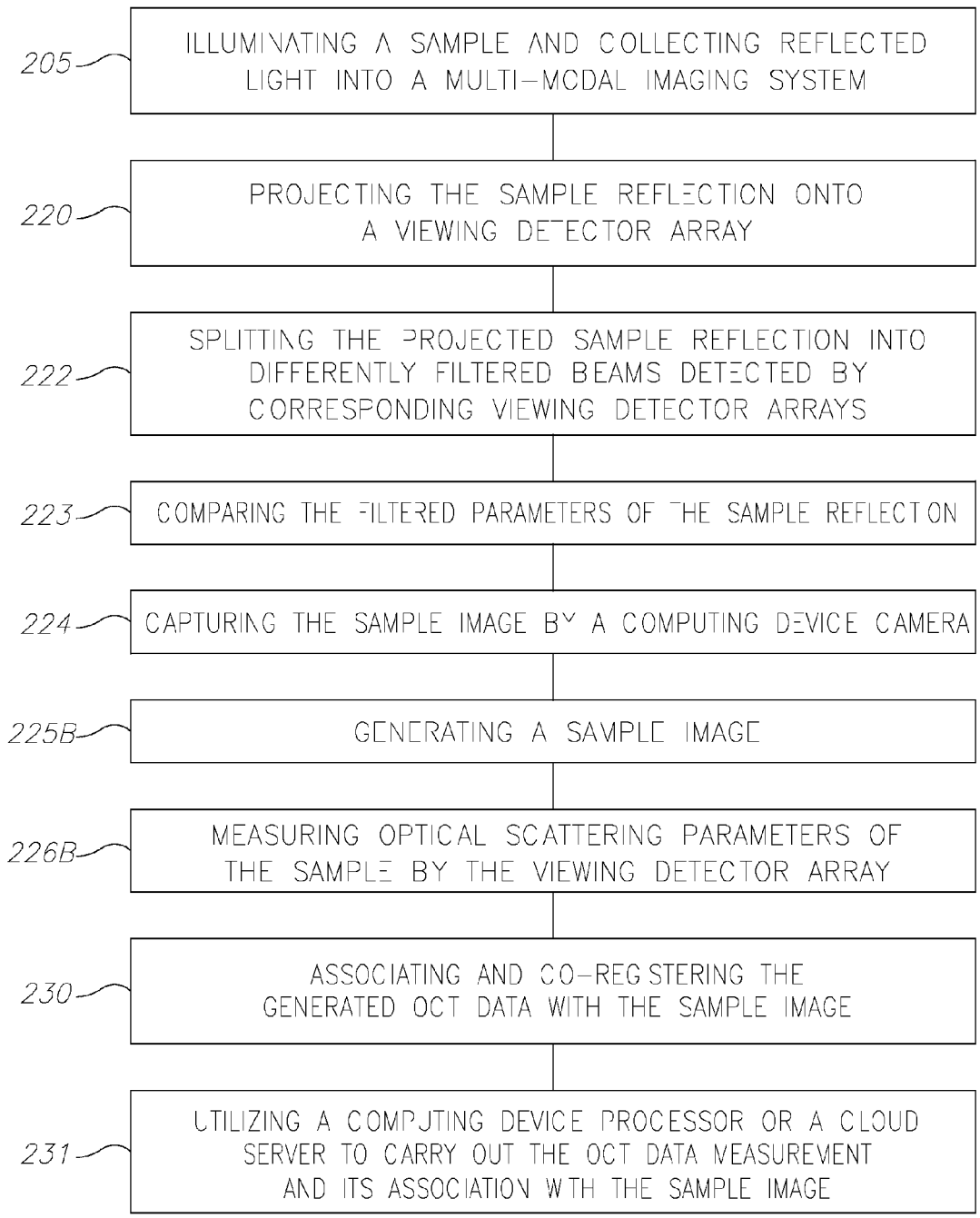

FIGS. 5A and 5B are high level schematic flowcharts illustrating an OCT method 200, according to some embodiments of the invention. FIG. 5A refers to OCT related stages, while FIG. 5B augment method 200 with stages relating to the multi modal image capturing.

OCT method 200 comprises illuminating the sample and collecting light reflected off the sample into a multimodal imaging system (stage 205). The reflected light may then be separated into an interferometric (OCT) track (illustrated in FIG. 5A) and tracks for non-interference based other modalities (illustrated in FIG. 5B). The OCT track begins by interfering a reflection from a sample with a reference beam to yield an interference pattern (stage 210), splitting the OCT light into various detection schemes (stage 212) based on various filter arrangements and comparing between them (stage 213), generating a sample OCT image (stage 225A), and measuring optical properties from the OCT data by an OCT detector array (stage 226A).

The non-OCT track begins by projecting the sample reflection onto a viewing detector array (stage 220), splitting the non-OCT light into various detection schemes (stage 222) based on various filter arrangements and comparing between them (stage 223), to generate a sample image (stage 225B), and measuring optical properties from the non-OCT data by a viewing detector array (stage 226B), and finally, associating and co-registering the generated OCT data with the sample image (stage 230).

Measuring the optical scattering properties (stages 226A, 226B) is carried out simultaneously and non destructively.

In embodiments, the interfering (stage 210) is carried out by a Michelson interferometer, by a Mach-Zehnder interferometer, or by other types of interferometers.

In embodiments, illuminating the sample and collected light reflected thereof (stage 205) comprises generating a depth profile by introducing a pathlength delay in the reference arm (time domain OCT), or from a plurality of monochromatic interference patterns generated either by sweeping a wavelength range of the interferometer (swept source OCT) or by including a dispersive element and spectrally sensitive detection (spectral domain OCT), as well as performing the various signal processing steps as necessary, including the inverse Fourier transform and Hilbert transform, to define depth ranges in the sample (stage 206). For the time domain and swept source configurations this can be done on point, line, or area measurements; for the spectral domain configuration, this can be done on point or line measurements.

In embodiments, OCT method 200 further comprises splitting the projected sample reflection into at least two differently filtered beams detected by at least two corresponding viewing detector arrays (stage 222), to compare the filtered parameters of the sample reflection (stage 223).

In embodiments, OCT method 200 further comprises splitting the interfered sample reflection and reference beam, into at least two differently filtered beams detected by at least two corresponding OCT detector arrays (stage 212), to compare the filtered parameters of the OCT data (stage 213).

In embodiments, OCT method 200 further comprises capturing the sample image by a computing device camera directly or indirectly connected to computing device (stage 224) and utilizing a computing device processor or a cloud server to carry out the OCT data measurement (stage 231) and its association with the sample image (stage 230). In case of a cloud server, method 200 further comprises communicating the images and data to and from the cloud server and carrying out the processing on the cloud server.

The inventor wishes to acknowledge the Whitaker International Program, administered by the Institute of International Education, for supporting the research that led to the above disclosed invention.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Embodiments of the invention may include features from different embodiments disclosed above, and embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. An Optical Coherence Tomography (OCT) system comprising:
    a light source arranged to generate a light beam projected onto a sample;
    an interferometer comprising a first beam splitter configured to split the light beam into an OCT track reference reflection beam and an OCT track sample reflection beam;
    an imaging unit comprising:
        (a) an OCT detector arranged to derive OCT data from the OCT track beams,
        (b) a second beam splitter arranged between the light source and the first beam splitter to generate a non-OCT track sample reflection beam, and
        (c) a viewing detector configured to generate a visual sample image from the non-OCT track sample reflection beam; and
    a signal processing unit arranged to:
        associate the OCT data with the visual sample image to generate multi modal measurements of the sample corresponding to at least one of a single scattering regime, a multiple scattering regime, and a light diffusion regime of the sample, and
        measure scattering parameters of the sample by modelling the OCT data as $\rho \exp(-\mu z)$, where:
            $\rho$ is a reflectivity given by $\mu_s\, b(g)\, \Delta z$, where:
                $\mu_s$ is a scattering coefficient, $b(g)$ is a fraction of backscattered light collected by an objective lens, $\Delta z$ is an axial resolution,
            $\mu$ is an attenuation given by $2G\, (\mu_s\, a(g)+\mu_a)$, where:
                G is a geometrical factor of an aperture of the objective lens, g is an anisotropy factor, $a(g)$ is a numerical factor describing how g affects focusing in a turbid medium, $\mu_a$ is an absorption coefficient,
            z is an axial value.
2. The OCT system of claim 1, wherein the viewing detector is a viewing detector array and the OCT detector is an OCT detector array, and the signal processing unit is arranged to yield multi modal images of the sample.
3. The OCT system of claim 1, wherein the viewing detector is arranged to measure any of: a scattering coefficient, an absorption coefficient, and an anisotropy factor of the sample.
4. The OCT system of claim 1, wherein the interferometer is configured as a common path interferometer.
5. The OCT system of claim 1, wherein the light beam incident on the sample is collimated.
6. The OCT system of claim 1, wherein the interferometer is configured as a Mach-Zehnder interferometer, wherein the reference reflection beam is generated from light split from the light beam.
7. The OCT system of claim 1, further comprising a wavelength range sweeping dispersive element configured to disperse the light beam to yield a monochromatic measurement beam, wherein the signal processing unit is further arranged to derive depth-resolved OCT data by integrating OCT data from the monochromatic measurement beams over the wavelength range.
8. The OCT system of claim 1, further comprising a wavelength range sweeping dispersive element configured to disperse the OCT track measurement beam to yield a wavelength separation of the OCT track measurement beam.
9. The OCT system of claim 1, wherein the projected sample reflection beam is split into at least two sample reflection beams that are each passed through different filters and detected by at least two corresponding viewing detectors, to compare the filtered parameters of the sample reflection beams.
10. The OCT system of claim 1, wherein the OCT track measurement beam is split into at least two OCT track measurement beams that are each passed through different filters and detected by at least two corresponding OCT detectors, to compare OCT data relating to the filtered parameters of the OCT track measurement beams.
11. The OCT system of claim 1, further comprising any of optical fibers and optical fiber bundles arranged to guide the light beam, the sample reflection beam, the reference reflection beam and the OCT track measurement beam.
12. The OCT system of claim 1, wherein the light source, the interferometer and the OCT detector are encased in a housing that is operably attachable to a computing device, and the signal processing unit is implemented in the computing device.
13. The OCT system of claim 1, wherein the viewing detector is a computing device camera.
14. An Optical Coherence Tomography (OCT) method comprising:
    projecting, using a light source, a light beam onto a sample;
    generating, from a sample reflection beam, a non-OCT track sample reflection beam, wherein the generating is performed using a second beam splitter arranged between the light source and a first beam splitter;
    generating, using the first beam splitter from the light beam, an OCT track measurement beam comprising an interference of the sample reflection beam with a reference reflection beam;
    projecting the non-OCT track sample reflection beam onto a viewing detector to generate a visual sample image;
    receiving the OCT track measurement beam at an OCT detector;
    deriving OCT data from the OCT track measurement beam;

associating and co-registering the generated OCT data with the visual sample image to yield multi modal measurements of the sample corresponding to at least one of a single scattering regime, a multiple scattering regime, and a light diffusion regime of the sample; and measuring scattering parameters of the sample by modelling the OCT data as $\rho \exp(-\mu z)$, where:

$\rho$ is a reflectivity given by $\mu_s\, b(g)\, \Delta z$, where:
$\mu_s$ is a scattering coefficient, $b(g)$ is a fraction of backscattered light collected by an objective lens, $\Delta z$ is an axial resolution, $\mu$ is an attenuation given by $2G\,(\mu_s\, a(g)+\mu_a)$, where:
G is a geometrical factor of an aperture of the objective lens, g is an anisotropy factor, $a(g)$ is a numerical factor describing how g affects focusing in a turbid medium, $\mu_a$ is an absorption coefficient, z is an axial value.

15. The OCT method of claim 14, further comprising measuring any of a scattering coefficient, an absorption coefficient, and an anisotropy factor of the sample.

16. The OCT method of claim 14, wherein generating the OCT track measurement beam is performed by any of a Michelson interferometer and a Mach-Zehnder interferometer.

17. The OCT method of claim 14, wherein measuring the OCT data comprises generating an image from a plurality of monochromatic images generated by at least one of: a time domain, a spectral domain, or a swept source OCT acquisition modes, to define a depth parameter of the sample.

18. The OCT method of claim 14, further comprising splitting the non-OCT track sample reflection beam into at least two differently filtered beams detected by at least two corresponding viewing detectors, to compare the filtered parameters of the sample reflection.

19. The OCT method of claim 14, further comprising splitting the OCT track measurement beam into at least two differently filtered OCT track measurement beams detected by at least two corresponding OCT detectors, to compare the filtered parameters of the OCT data.

20. The OCT method of claim 14, further comprising capturing the visual sample image by a computing device camera and utilizing a computing device processor to carry out the OCT data measurement and its association with the visual sample image.

* * * * *